United States Patent [19]
Schwarz et al.

[11] Patent Number: 5,641,905
[45] Date of Patent: Jun. 24, 1997

[54] SECOND DERIVATIVE RESONANT ULTRASOUND RESPONSE ANALYZER

[75] Inventors: James J. Schwarz, Albuquerque; David E. Thomas, Peralta, both of N.M.

[73] Assignee: Quatro Corporation, Albuquerque, N.M.

[21] Appl. No.: 572,745

[22] Filed: Dec. 14, 1995

[51] Int. Cl.$^6$ ............... G01N 29/12; G01H 13/00
[52] U.S. Cl. ............... 73/579; 73/602; 73/659
[58] Field of Search ............... 73/579, 602, 646, 73/659, 627, 628

[56] References Cited

U.S. PATENT DOCUMENTS

| | | | |
|---|---|---|---|
| 4,976,148 | 12/1990 | Migliori et al. | 73/579 |
| 5,062,296 | 11/1991 | Migliori | 73/579 |
| 5,150,617 | 9/1992 | Schwarz et al. | 73/579 |
| 5,351,543 | 10/1994 | Migliori et al. | 73/579 |
| 5,355,731 | 10/1994 | Dixon et al. | 73/579 |
| 5,408,880 | 4/1995 | Rhodes et al. | 73/579 |
| 5,425,272 | 6/1995 | Rhodes et al. | 73/579 |

*Primary Examiner*—Hezron E. Williams
*Assistant Examiner*—Helen C. Kwok
*Attorney, Agent, or Firm*—Ronald R. Snider

[57] ABSTRACT

A method is provided for detecting resonant ultra sound (RUS) Spectroscopy peaks which is based upon taking the second derivative of the RUS spectrum. The second derivative provides a more sensitive analysis tool, and makes it possible to separate and distinguish peaks in the spectrum which are not readily discernable by other analyses of the spectrum. Analysis criteria such as cut off heights and Z-widths provide judgment criteria for identification of resonant peaks.

14 Claims, 6 Drawing Sheets

SECOND DERIVATIVE RESONANT ULTRASOUND RESPONSE ANALYZER

BACKGROUND OF THE INVENTION

1. Field of the Invention

In the practice of resonant ultra sound RUS measurement, as illustrated in U.S. Pat. Nos. 4,976,148, 5,355,731, 5,408, 880, 5,062,296, 5,351,543, and 5,425,272 and U.S. patent applications Ser. Nos. 08/075,159, 08/520,009 and 08/409, 218 (all which are incorporated herein by reference), there is a need for identification for resonant frequencies of parts which are to be tested. Once a resonant frequency has been identified either mathematically, or by testing similar parts, then further testing can be conducted more efficiently.

2. The Prior Art

In the measurement technique directed to split degeneracies as described in U.S. Pat. No. 5,355,731 and in U.S. patent application Ser. No. 08/075,159, splitting of degeneracies was observed by merely viewing the response of the object i.e. the amplitude of the response as a function of frequency.

BRIEF SUMMARY OF THE INVENTION

This invention finds utility in two specific areas. The first is in identifying the resonant frequency of a part, and the second is in analyzing the resonant ultra sound (RUS) response.

The use of the second derivative picker of this invention enables one to identify resonant peaks in a part undergoing RUS inspections in a different and more precise manner than the techniques here before known in the prior art. In this invention, the use of the second derivative of the response permits separation of degeneracies which are close together, and detection of small splits in degeneracies. In the prior art, only large splitting of the degeneracy could be observed by looking at the spectra of frequency versus amplitude. Here, with the second derivative of frequency versus amplitude, a much more sensitive and powerful tool is obtained. In the prior art, only the magnitude of the peaks was considered. There is no consideration of the width of a peak, or of the derivatives of the magnitude.

The method of measurement in accordance with this invention comprises the steps of subjecting an object to RUS over a range of frequencies; detecting a resonant response of said object to said RUS; analyzing only said detected resonant response with a second derivative peak picker to pick at least one frequency where a peak resonant response of said object occurs; subjecting another object to RUS at said frequency where said peak resonant response occurred, and determining acceptability of said another object based upon response of said another object to said RUS applied at said peak resonant response frequency.

DETAILED DESCRIPTION

This invention relates to a new peak-picking method based on taking the second derivative of the Resonant Ultra Sound (RUS) spectrum. This method of RUS has been developed to be capable of picking subtle peaks that have escaped previous methods. This method is also useful for identifying non-peaks, or frequencies where testing is not required. The method works by looking for the largest-magnitude negative values of the 2 nd derivative in a spectrum, and checking the width of the 2 nd-derivative minima.

The new 2 nd Derivative method is based on an analytical combination of the operations of smoothing and differentiation. Because these operations are at cross-purposes to one another (smoothing involves adding elements of the spectrum magnitude array, while differentiation involves subtraction of these elements), considerable simplification results when these operations are analytically combined before computation. If the original voltage-magnitude array is referred to as $V_i$, i=1,2, . . . NPTS, and the number of smoothing points per side as NS, then the 'smoothed' array $U_i$ can be written as:

$$U_i = \frac{\sum_{j=i-NS}^{i+NS} V_j}{2NS+1} \qquad \text{(Eq. 1)}$$

The derivative of the raw waveform is defined as:

$$\frac{dVi}{df} = \frac{V(i+1) - V(i-1)}{2\Delta f}, \qquad \text{(Eq. 2)}$$

where $\Delta f$ is the change in frequency from one point to the next. When Eq. 1 and Eq. 2 are combined, the result for the derivative of a smoothed spectrum, after cancellation of terms and simplification, can be written as:

$$\frac{dUi}{df} = U'i = \frac{U(i+1) - U(i-1)}{2\Delta f} = $$

$$\frac{-V(i-NS-1) - V(i-NS) + V(i+NS) + V(i+NS+1)}{2\Delta f (2NS+1)} \qquad \text{(Eq. 3)}$$

The proof that the derivative of the smoothed spectrum is identical to a smoothing of the raw derivative is left to the reader. The 1 st derivative only depends on 4 points of the original, raw spectrum, no matter how many smoothing points are used. In fact, smoothing amounts to just a widening of the gap between data points used. For no smoothing (NS=0), Eq. 3 reduces down to Eq. 2.

The calculation of the second derivative proceeds in a similar fashion, and has the form shown in Eq. 4. The 2 nd derivative depends on just 8 points of the original raw spectrum, independently of how many smoothing points are used.

$$\frac{d^2 Ui}{df^2} = \frac{U'(i+1) - U'(i-1)}{2\Delta f} = $$

$$\frac{V(i-NS-2) + V(i-NS-1) +}{V(i+NS+1) + V(i+NS+2)} - $$
$$\frac{V(i-NS) + V(i-NS+1) + V(i+NS-1) + V(i+NS)}{(2\Delta f)^2 (2NS+1)} \qquad \text{(Eq. 4)}$$

Because the operations of smoothing and differentiation are combined, considerable acceleration of the peak-finding process can be obtained. The data do not have to be smoothed prior to differentiation, nor does the 1 st derivative need to be calculated. Once the raw data have been obtained, a single pass through these data with Eq. 4 provides enough information to pick the peaks.

Figure 1:
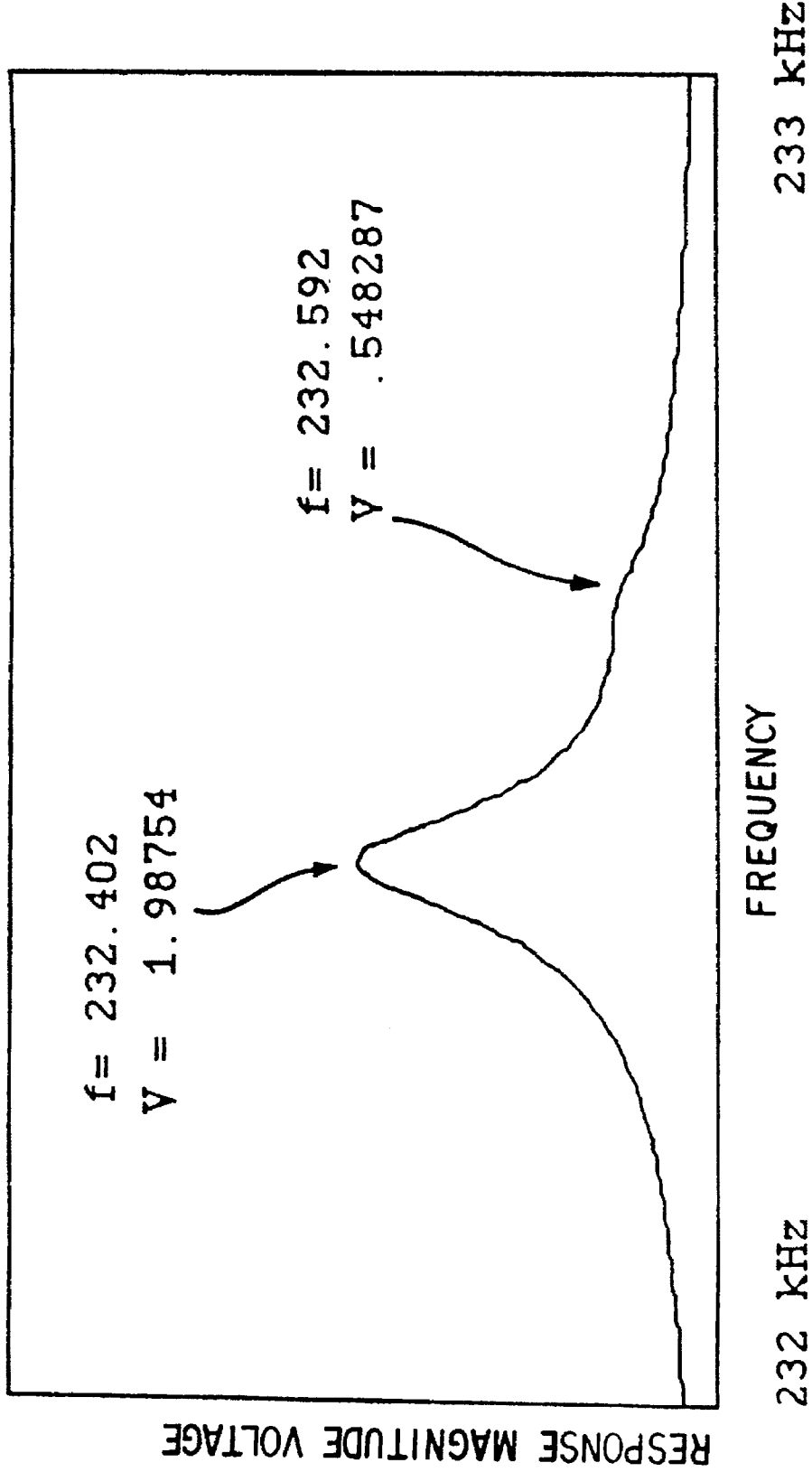
FIG. 1 shows a typical RUS spectrum (simulated).
Figure 2:
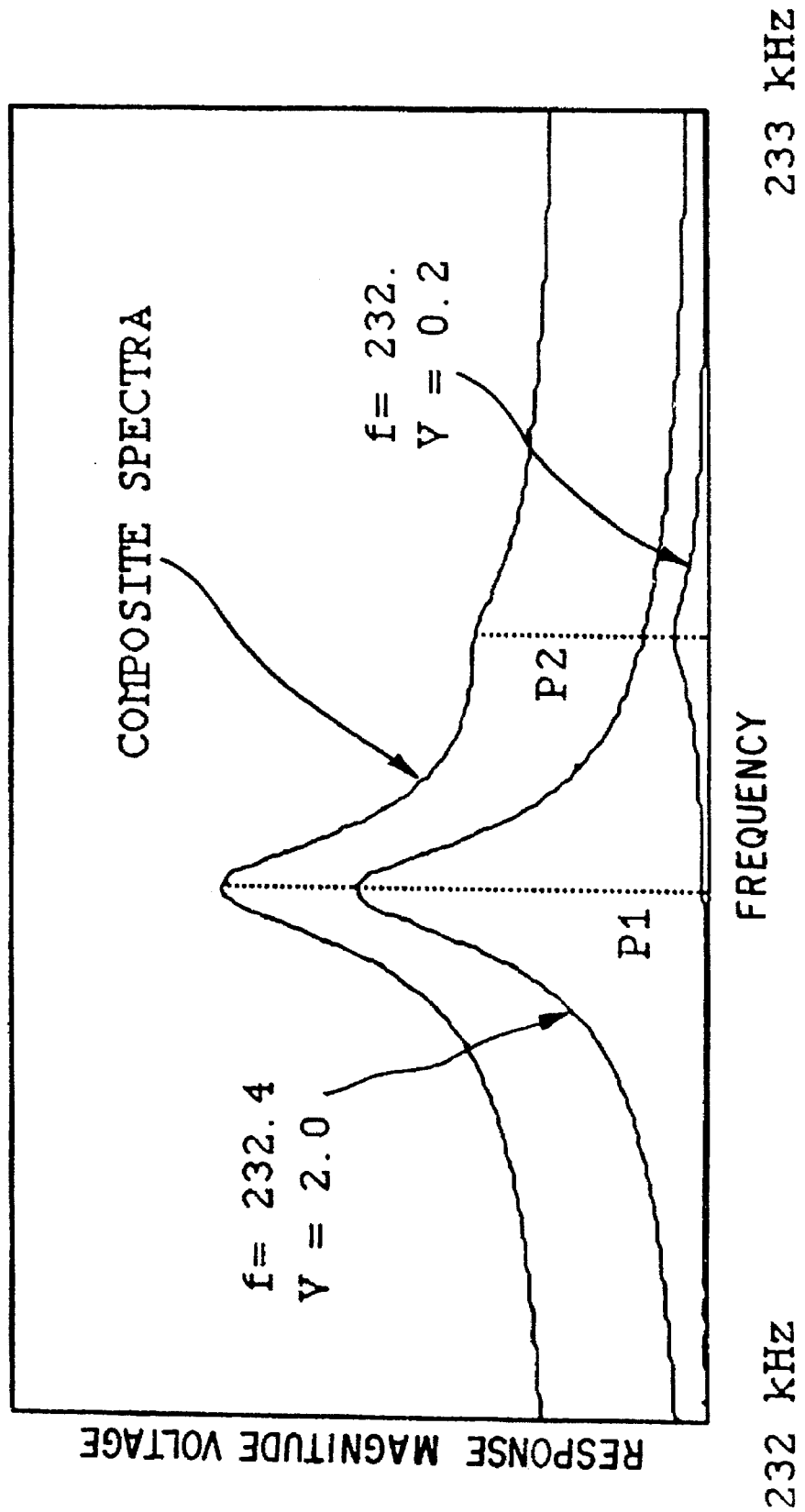
FIG. 2 shows composite resonance peaks (simulated) of the spectrum of FIG. 1.
Figure 3:
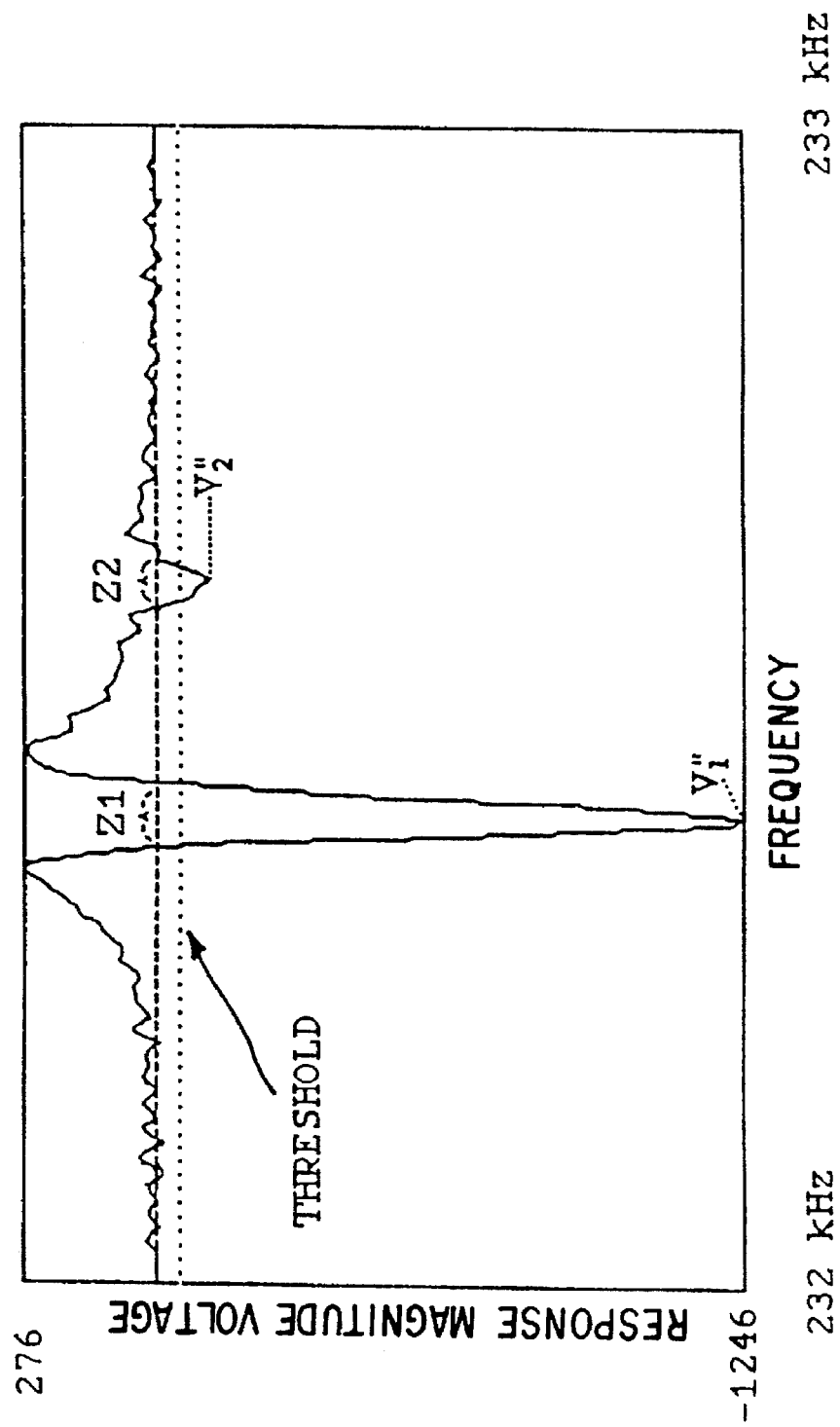
FIG. 3 shows a second derivative of the spectrum (simulated).

A diagram of a 2 nd derivative of a typical RUS spectrum appears in FIG. 1. The raw spectrum appears at the bottom of FIG. 1, and contains one main peak, and a slight split peak on the shoulder. The spectrum is actually a composite of two individual resonances, as shown in FIG. 2. The 2 nd derivative of the data in FIG. 1 is plotted in FIG. 3. One figure of merit for peak location is the magnitude of the second derivative. As the figure shows, the largest-magnitude (negative) values of the 2 nd derivative, labeled $V''_1$ and $V''_2$, correspond to the locations of the peaks. The other important variable is the widths of 2 nd-derivative zero-crossings, labeled $Z_1$ and $Z_2$. The benefit of the new method arises because it is much easier to locate the large negative 2 nd-derivative peaks than it is to extract them from subtle inflections in the raw data. Suitable bounds on zero-crossing width can prevent picking of spurious, low-level or noise-induced peaks.

Figure 4:
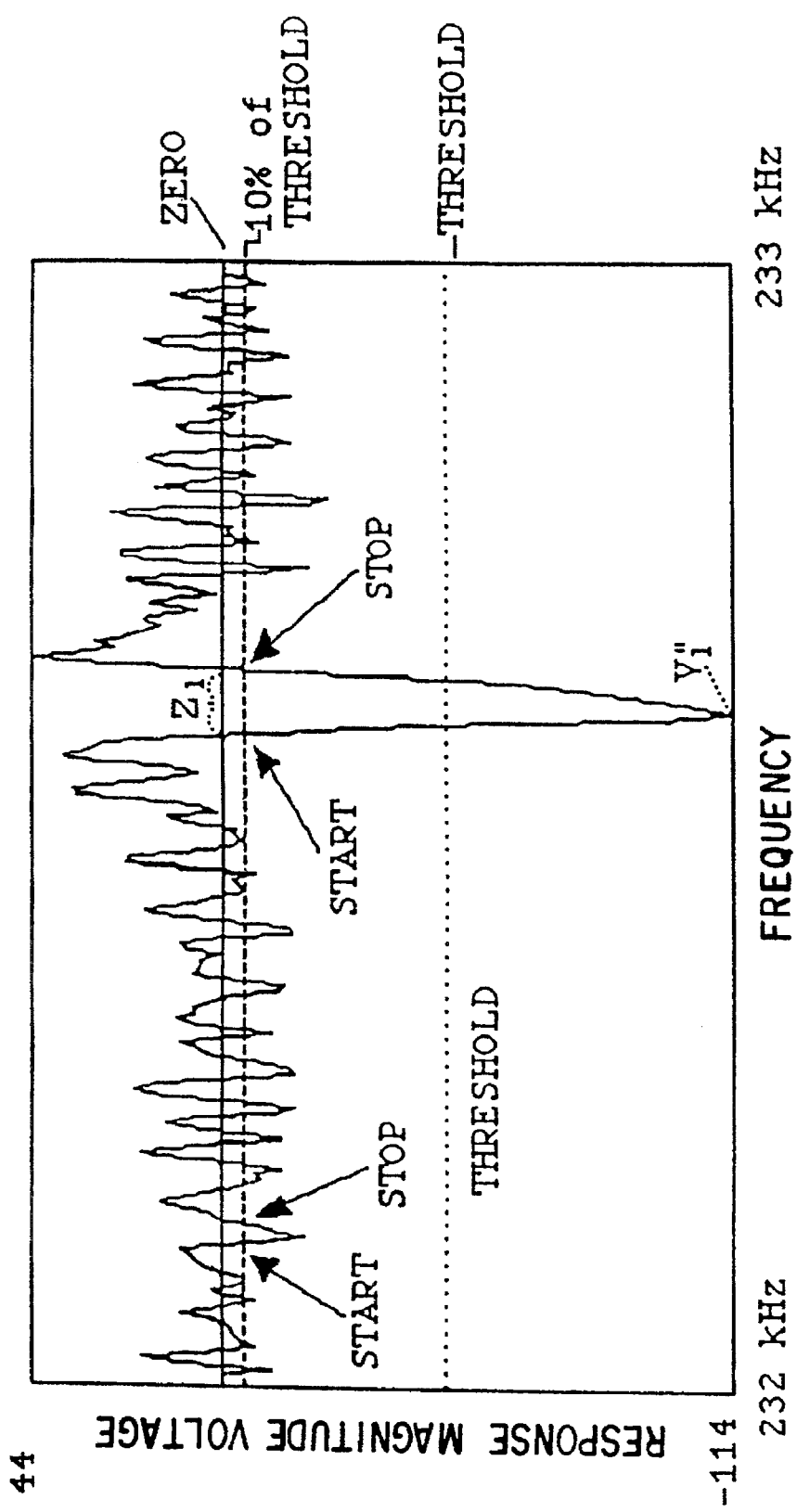
FIG. 4 shows a detail second derivative spectrum (simulated).

The new algorithm has been coded as follows. Three parameters must be supplied: the number of points for smoothing (NS), a threshold (CUTOFF) for discrimination against small peaks, and a zero-crossing width (ZWIDTH) for discrimination against noise peaks. The raw data array is analyzed, and the 2 nd derivative is calculated for each point (using Eq. 4). As soon as the 2 nd derivative data drops below 10% of the threshold, a flag for a potential peak is set as TRUE, and the frequency for what will be the left side of the zero-crossing is calculated with interpolation. FIG. 4 shows two such starting points (out of many), both labeled "START". The sweep through the data continues, and the index (data point number) and value of the largest-magnitude 2 nd derivatives are stored in memory. When the 2 nd derivative rises above 10% of the threshold, the frequency for the right side of the zero-crossing is calculated with interpolation. FIG. 4 shows two such ending points (out of many), both labeled "STOP". The largest 2 nd derivative in the interval (from START to STOP) is compared to the threshold, or CUTOFF. In addition, the width of the zero-crossing, equal to frequency (STOP)—frequency(START), is compared to the nominal zero-crossing value (ZWIDTH). If both the largest-magnitude 2 nd derivative exceeds CUTOFF, and the zero-crossing width exceeds ZWIDTH, then the frequency at which the maximum 2 nd derivative was logged is set as the peak frequency, and the array of peaks is incremented. In any event (peak or no peak), the flag for a potential peak is set as FALSE, and the search goes on until the end of the data is reached.

Only the top few peaks are kept in a working array, and these are ordered from largest-magnitude to smallest. The limit of working peaks is normally less than 10 but the algorithm can accommodate more simply by changing the number NMAX of desired peaks.

Figure 5:
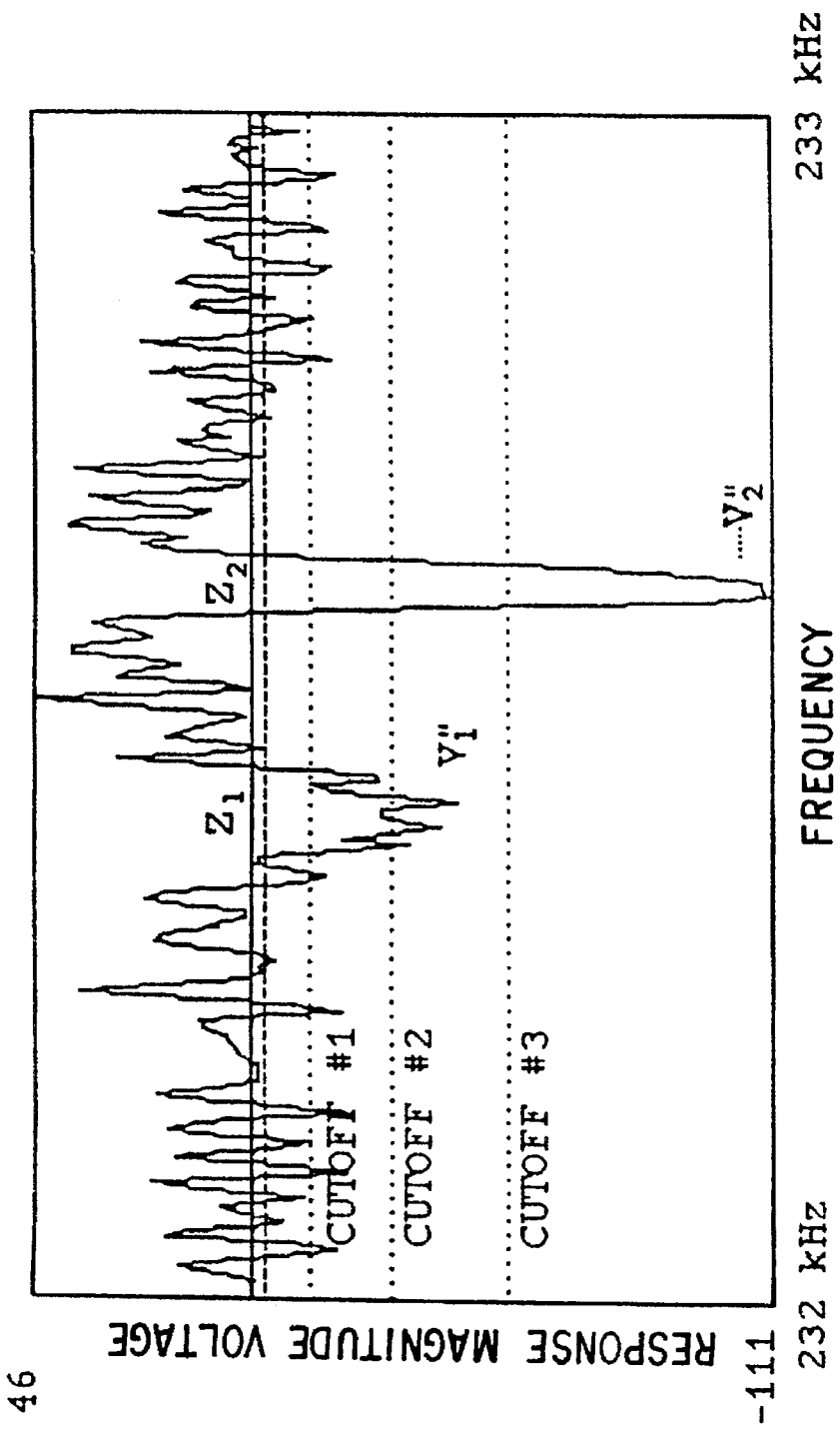
FIG. 5 shows different cutoffs and the effect of changing the zero crossing width.

FIG. 5 provides examples of peak-acceptance tests. Three possible values for CUTOFF are indicated (#1, #2, and #3). In several locations, the level for CUTOFF #1 is exceeded by the data; however, these candidate peaks will have very small zero-crossing widths, and should be rejected on that basis. Only two areas have 2 nd derivative values that exceed CUTOFF #2; the corresponding values are labeled $V''_1$ and $V''_2$. Even though the magnitude of $V''_1$ is smaller than that for $V''_2$, the zero-crossing for peak #1 ($Z_1$) is larger than that for peak #2 ($Z_2$). It is clear that increasing the CUTOFF from CUTOFF #2 to CUTOFF #3 would eliminate Peak #1; but, reducing the value of ZWIDTH, with CUTOFF #2, could eliminate Peak #2 and retain #1. The two parameters are powerful tools for peak selection.

Figure 6:
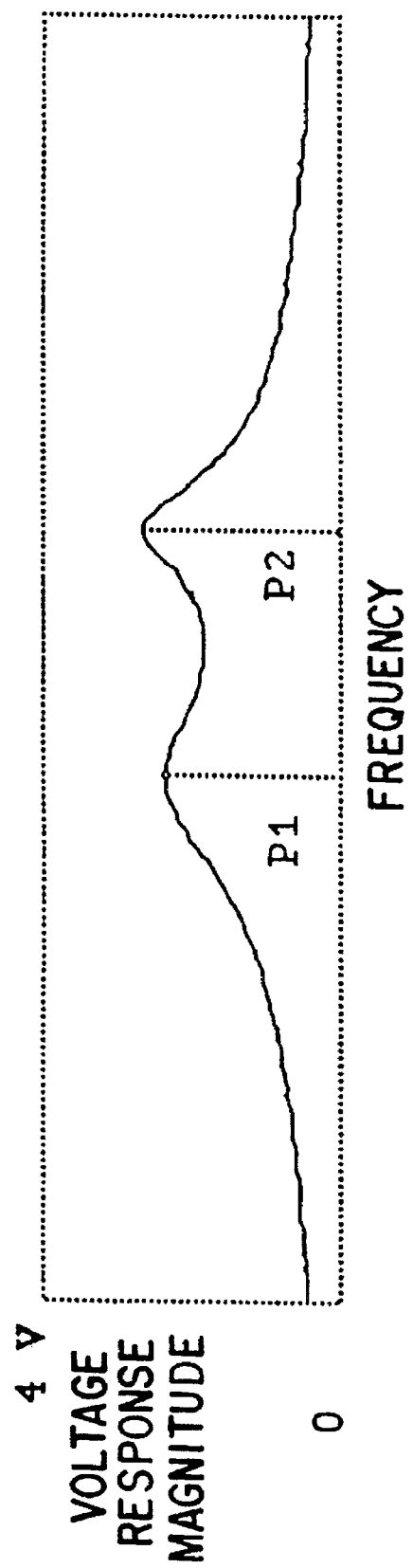
FIG. 6 shows composite resonance for raw data of FIG. 5 (simulated).

The raw data corresponding to the 2 nd derivative spectrum of FIG. 5 appear in FIG. 6. Note that the narrower peak, P2, has a much larger-magnitude 2 nd derivative than Peak #1 (P1), even though both have similar amplitudes.

The input parameters can be estimated as follows: The CUTOFF value can be estimated by consideration of the analytical derivative of an ideal Lorentzian. The ZWIDTH parameter should be less than the full-width at half-maximum power (FWHM) of the peak.

An ideal Lorentzian spectrum is defined in Eq. 5. The peak frequency is $f_0$, the FWHM is H, and the peak amplitude (raw voltage) is A. The first derivative appears in Eq. 6, and the second derivative in Eq. 7. The value of the second derivative fight at the peak frequency is proportional to peak amplitude, A, and inversely proportional to the square of the FWHM, H.

$$V(f) = A \left[ 1 + \frac{4(f-f_0)^2}{H^2} \right]^{-1/2} \qquad (\text{Eq. 5})$$

$$V'(f) = \frac{-4A}{H^2} (f-f_0) \left[ 1 + \frac{4(f-f_0)^2}{H^2} \right]^{-3/2} \qquad (\text{Eq. 6})$$

$$V''(f) = \frac{-4A}{H^2} \left[ 1 + \frac{4(f-f_0)^2}{H^2} \right]^{-3/2} \left[ 1 - \frac{12(f-f_0)^2}{H^2 + 4(f-f_0)^2} \right] \qquad (\text{Eq. 7})$$

$$V''(f_0) = \frac{-4A}{H^2} \qquad (\text{Eq. 8})$$

Thus, the value for CUTOFF can be estimated easily with Eq. 8. In practice, applicant has found good results for values of CUTOFF at about 1/10th to 1/2 of the Eq. 8 result.

We claim:

1. A method of resonant ultrasound (RUS) testing comprising the steps of:
    subjecting an object to RUS over a range of frequencies;
    detecting a resonant response of said object to said RUS;
    analyzing only said detected resonant response by taking a second derivative with a second derivative peak picker to pick at least one frequency where a peak resonant response of said object occurs;
    subjecting another object to RUS at said frequency where said peak resonant response occurred; and
    determining acceptability of said another object based upon response of said another object to said RUS applied at said peak resonant response frequency.

2. A method in accordance with claim 1 wherein said peak picker is responsive to negative values of a second derivative spectrum.

3. A method in accordance with claim 1 wherein said peak picker is responsive to Z-width of negative values of said second derivative.

4. A method in accordance with claim 1 wherein said peak picker is responsive to magnitude of negative values of said second derivative.

5. A method in accordance with claim 1 wherein said second derivative peak picker includes a smoothing function.

6. A method in accordance with claim 1 comprising the step of subjecting said object to RUS over a range of frequencies including a frequency where a degeneracy is expected to occur and detecting a peak resonant response with said second derivative peak picker to detect splitting of degeneracies of the resonant response.

7. A method in accordance with claim 4 wherein a cut off value is estimated by the following relationship:

$$V''(f_0) = \frac{-4A}{H^2}$$

where V" is the second derivative of the voltage response magnitude, $f_0$ is the peak frequency, H is the full width at half-maximum power of the peak, and A is the raw voltage.

8. A method of RUS testing an object for split degeneracies comprising the steps of:
  subjecting said object to said RUS;
  detecting a resonant response of said object;
  analyzing only said response by taking a second derivative with a second derivative peak picker to identify splitting of degeneracies.

9. A method in accordance to claim 8 wherein said second derivative peak picker includes a smoothing function.

10. A method in accordance to claim 8 comprising the step of subjecting said object to said RUS at a frequency where a degeneracy is expected to occur and detecting a response at said frequency where a degeneracy is expected with said second derivative peak picker to detect splitting of degeneracies.

11. A method in accordance with claim 8 wherein said second derivative peak picker is responsive to threshold levels of second derivative response.

12. The method in accordance with claim 11 wherein said response is the Zero-crossing width criteria.

13. The method in accordance with claim 11 wherein said threshold levels are the magnitude of the response.

14. A method in accordance with claim 13 wherein a cut off value is estimated by the following relationship:

$$V''(f_0) = \frac{-4A}{H^2}$$

where V" is the second derivative of the voltage response magnitude $f_0$ is the peak frequency, H is the full width at half-maximum power of the peak, and A is the raw voltage.

* * * * *